US00PP17795P2

(12) United States Plant Patent
Dekker

(10) Patent No.: US PP17,795 P2
(45) Date of Patent: Jun. 12, 2007

(54) *CHRYSANTHEMUM* PLANT NAMED 'DEKPESO'

(50) Latin Name: *Chrysanthemum×morifolium*
Varietal Denomination: Dekpeso

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 3 days.

(21) Appl. No.: 11/267,905

(22) Filed: Nov. 4, 2005

(51) Int. Cl.
*A01H 5/00* (2006.01)

(52) U.S. Cl. ..... Plt./294

(58) Field of Classification Search ..... Plt./294, Plt./286

See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Dekpeso', characterized by its large anemone-type inflorescences with elliptic-shaped, white-colored ray florets and yellowish green-colored disc florets; strong, upright and freely branching flowering stems; early and uniform flowering response; and good postproduction longevity.

2 Drawing Sheets

Botanical designation: *Chrysanthemum×morifolium.*
Cultivar denomination: 'Dekpeso'.

BACKGROUND OF THE INVENTION

The present invention relates to a new and distinct cultivar of *Chrysanthemum* plant, botanically known as *Chrysanthemum×morifolium* and referred to by the name 'Dekpeso'.

The new *Chrysanthemum* is the product of a planned breeding program conducted by the Inventor in Hensbroek, The Netherlands. The objective of the breeding program is to create new cut *Chrysanthemum* cultivars with interesting inflorescence forms and attractive floret coloration.

The new *Chrysanthemum* originated from a cross-pollination made by the Inventor on Nov. 14, 2002, in Hensbroek, The Netherlands, of a proprietary selection of *Chrysanthemum* identified as code number 99.795,01, not patented, as the female, or seed, parent with a proprietary *Chrysanthemum* selection identified as code number 01.5602,01, not patented, as the male, or pollen, parent. The new *Chrysanthemum* was discovered and selected by the Inventor as a single plant within the progeny of the stated cross-pollination in a controlled environment in Hensbroek, The Netherlands.

Asexual reproduction of the new *Chrysanthemum* by terminal cuttings in Hensbroek, The Netherlands since December, 2002, has shown that the unique features of this new *Chrysanthemum* are stable and reproduced true to type in successive generations.

BRIEF SUMMARY OF THE INVENTION

The cultivar Dekpeso has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekpeso'.

These characteristics in combination distinguish 'Dekpeso' as a new and distinct cultivar:

1. Large anemone-type inflorescences with elliptic-shaped, white-colored ray florets and yellowish green-colored disc florets.
2. Strong, upright and freely branching flowering stems.
3. Early and uniform flowering response.
4. Good postproduction longevity.

Plants of the new *Chrysanthemum* can be compared to plants of the female parent selection. In side-by-side comparisons conducted in Hensbroek, The Netherlands, plants of the new *Chrysanthemum* differed from plants of the female parent selection in the following characteristics:

1. Plants of the new *Chrysanthemum* were more vigorous than plants of the female parent selection.
2. Plants of the new *Chrysanthemum* had larger and more durable leaves than plants of the female parent selection.
3. Plants of the new *Chrysanthemum* had larger inflorescences than plants of the female parent selection.

Plants of the new *Chrysanthemum* can be compared to plants of the male parent selection. In side-by-side comparisons conducted in Hensbroek, The Netherlands, plants of the new *Chrysanthemum* differed from plants of the male parent selection in the following characteristics:

1. Plants of the new *Chrysanthemum* were less vigorous than plants of the male parent selection.
2. Plants of the new *Chrysanthemum* and the male parent selection differed in inflorescence form as plants of the male parent selection had daisy-type inflorescences.

Plants of the new *Chrysanthemum* can be compared to plants of the *Chrysanthemum* cultivar Dekchop, not patented. In side-by-side comparisons conducted in Hensbroek, The Netherlands, plants of the new *Chrysanthemum* differed primarily from plants of the cultivar Dekchop in the following characteristics:

1. Plants of the new *Chrysanthemum* were taller than plants of the cultivar Dekchop.

2. Plants of the new *Chrysanthemum* had larger inflorescences than plants of the cultivar Dekchop.
3. Plants of the new *Chrysanthemum* had more ray florets per inflorescence than plants of the cultivar Dekchop.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph on the first sheet comprises a side perspective view of a typical flowering stem of 'Dekpeso'.

The photograph at the top of the second sheet is a close-up view of typical inflorescences of 'Dekpeso'.

The photograph at the bottom of the second sheet is a close-up view of upper and lower surfaces of typical inflorescences and leaves of 'Dekpeso'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the summer in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about nine weeks from planting when the photographs and the description were taken.

Botanical classification: *Chrysanthemum×morifolium* cultivar Dekpeso.

Commercial classification: Anemone-type *Chrysanthemum* typically grown as a spray-type cut flower.

Parentage:

*Female or seed parent.*—Proprietary selection of *Chrysanthemum×morifolium* identified as code number 99.975,01, not patented.

*Male or pollen parent.*—Proprietary selection of *Chrysanthemum×morifolium* identified as code number 01.5602,01, not patented.

Propagation:

*Type.*—Terminal tip cuttings.

*Time to initiate roots, summer.*—About 6 days at 20° C.

*Time to initiate roots, winter.*—About 7 days at 20° C.

*Time to produce a rooted cutting, summer.*—About 14 days at 20° C.

*Time to produce a rooted cutting, winter.*—About 16 days at 20° C.

*Root description.*—Fine; light brown in color.

*Rooting habit.*—Freely branching.

Plant description:

*Appearance.*—Herbaceous anemone-type cut *Chrysanthemum;* typically grown as a spray-type; erect and strong flowering stems. Moderately vigorous growth habit. Freely flowering growth habit.

*Flowering stem description.*—Length: About 70 cm to 80 cm. Diameter: About 6 mm. Strength: Strong. Texture: Pubescent. Aspect: Erect. Color: 146A.

*Foliage description.*—Arrangement: Alternate, simple. Length: About 6 cm to 15 cm. Width: About 3.5 cm to 9 cm. Apex: Cuspidate. Base: Attenuate. Margin: Pinnately lobed. Texture, upper and lower surface: Pubescent. Petiole length: About 1 cm to 2.5 cm. Color: Developing foliage, upper surface: 137A. Developing foliage, lower surface: Close to 147B. Fully expanded foliage, upper surface: Close to 147A; venation, 147B. Fully expanded foliage, lower surface: Close to 147B; venation, 147B. Petiole, upper and lower surfaces: 137C.

Inflorescence description:

*Appearance.*—Anemone-type inflorescence form with elliptic-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about seven later. Early and uniform flowering response.

*Postproduction longevity.*—Cut inflorescences will maintain good substance and form for about three weeks.

*Quantity of inflorescences per flowering stem.*—Freely flowering; grown as a spray-type, about 10 to 12 inflorescences develop per flowering stem.

*Inflorescence size.*—Diameter: About 7 cm to 8 cm. Depth (height): About 2.5 cm to 3 cm. Diameter of disc: About 3 cm.

*Inflorescence buds.*—Height: About 6 mm to 7 mm. Diameter: About 1 cm. Shape: Oblate. Color: 137B to 137C.

*Ray florets.*—Length: About 2.5 cm to 3.5 cm. Width: About 9 mm to 11 mm. Shape: Elliptic. Apex: Emarginate to cuspidate. Base: Attenuate; fused. Margin: Entire. Texture, upper and lower surfaces: Smooth, glabrous; satiny. Number of ray florets per inflorescence: About 30. Color: When opening, upper and lower surfaces: Close to 155D. Fully opened, upper and lower surfaces: Close to 155D.

*Disc florets.*—Shape: Tubular; enlarged. Length: About 8 mm to 15 mm. Width: About 1 mm to 3 mm. Number of disc florets per inflorescence: About 100. Color: Immature: 145C. Mature: Apex: 5A to 5B. Mid-section: 155A. Base: 145C to 145D.

*Phyllaries.*—Shape: Deltoid. Apex: Acute. Base: Truncate. Margin: Entire. Texture, upper surface: Smooth, glabrous. Texture, lower surface: Pubescent. Color, upper surface: Close to 146A. Color, lower surface: Close to 147A to 147B.

*Peduncles.*—Length, terminal peduncle: About 5 cm. Length, fourth peduncle: About 8 cm. Diameter: About 2 mm to 3 mm. Angle: About 45° from vertical. Strength: Moderately strong. Texture: Pubescent. Color: 137C.

*Reproductive organs.*—Androecium: No anthers observed on disc florets. Gynoecium: Present on both ray and disc florets. Stigma length: About 5 mm. Stigma diameter: About 0.3 mm. Stigma color: 150B.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Dekpeso', as illustrated and described.

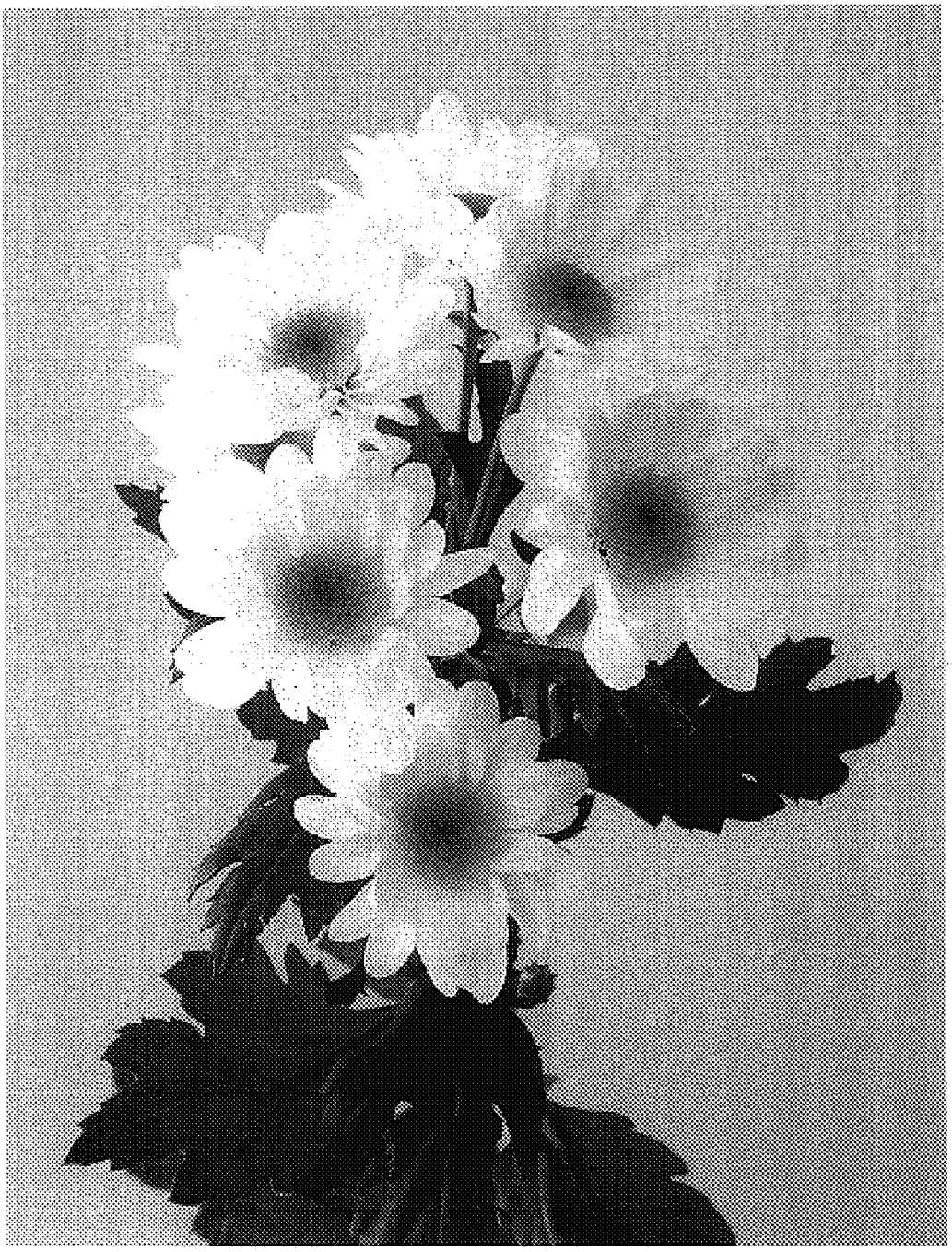

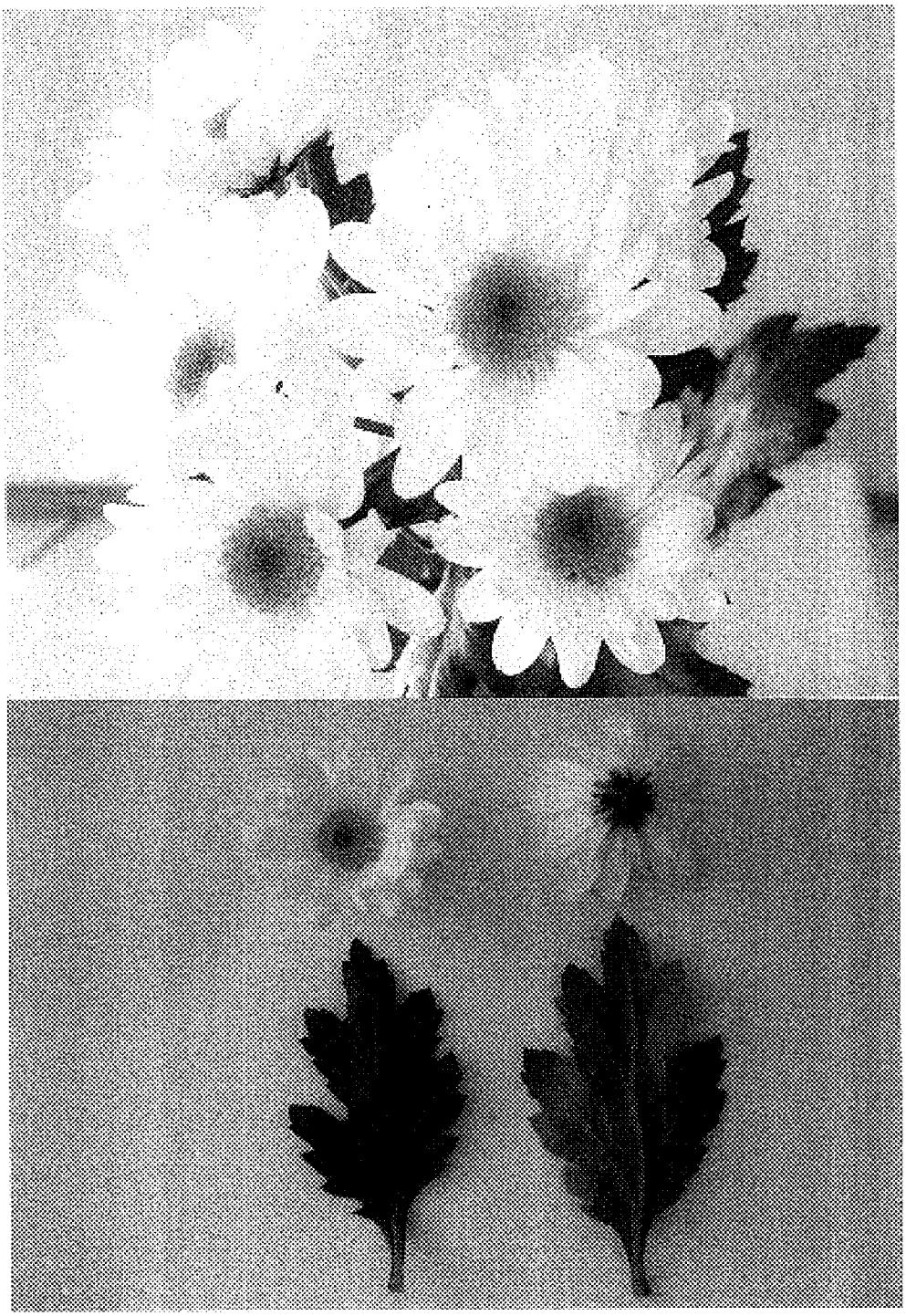

* * * * *